United States Patent [19]

Beck et al.

[11] Patent Number: 5,063,938
[45] Date of Patent: Nov. 12, 1991

[54] RESPIRATION-SIGNALLING DEVICE

[76] Inventors: Donald C. Beck, 18 Wood Glen Way, Boonton, N.J. 07005; Peter R. Mick, 4 Stonybrook Trail, Kinnelon, N.J. 07405

[21] Appl. No.: 607,675

[22] Filed: Nov. 1, 1990

[51] Int. Cl.$^5$ ............................................. A61B 5/08
[52] U.S. Cl. ...................................... 128/724; 128/10; 128/200.26; 128/202.22; 128/719; 73/204.15
[58] Field of Search ................. 128/10, 664, 719, 718, 128/724, 200.24, 200.26, 202.22; 604/318; 73/204.17, 204.15, 204.11

[56] References Cited

U.S. PATENT DOCUMENTS

| | | | |
|---|---|---|---|
| 2,831,181 | 4/1958 | Warner | 128/724 |
| 3,241,549 | 3/1966 | Tyler | 128/724 |
| 3,316,902 | 5/1967 | Winchel et al. | 128/724 X |
| 3,645,133 | 2/1972 | Simeth et al. | 73/204.15 |
| 3,648,518 | 3/1972 | Hans et al. | 73/204.15 |
| 3,884,219 | 5/1975 | Richardson et al. | 128/724 |
| 3,903,875 | 9/1975 | Hughes | 73/204.15 X |
| 4,176,660 | 12/1979 | Mylrea et al. | 128/724 X |
| 4,363,238 | 12/1982 | Willam | 128/724 X |
| 4,366,821 | 1/1983 | Wittmaier et al. | 128/724 X |
| 4,420,001 | 12/1983 | Hearne | 128/724 |
| 4,450,719 | 5/1984 | Nishimura et al. | 73/204.15 |
| 4,627,840 | 12/1986 | Cuadra et al. | 604/151 |
| 4,648,396 | 3/1987 | Raemer | 128/204.22 |
| 4,651,746 | 3/1987 | Wall | 128/670 |
| 4,665,385 | 5/1987 | Henderson | 340/539 |
| 4,749,553 | 7/1988 | Lopez | 422/84 |
| 4,756,670 | 7/1988 | Arai | 417/43 |
| 4,777,963 | 10/1988 | McKenna | 128/724 |
| 4,790,327 | 12/1988 | Despotis | 128/719 |
| 4,803,471 | 2/1989 | Rowland | 340/626 |
| 4,815,459 | 3/1989 | Beran | 128/207.14 |
| 4,852,563 | 8/1989 | Gross | 128/202.27 |
| 4,852,583 | 8/1989 | Walker | 128/716 |
| 4,924,876 | 5/1990 | Cameron | 128/725 |

FOREIGN PATENT DOCUMENTS

| | | | |
|---|---|---|---|
| 2575917 | 1/1985 | France | 128/724 |
| 1110440 | 8/1984 | U.S.S.R. | 128/724 |
| 1080982 | 8/1967 | United Kingdom | 128/724 |
| 8802819 | 4/1988 | World Int. Prop. O. | 128/719 |

OTHER PUBLICATIONS

"Battery Operated Respiratory Phase Detector System"; New Electronics, vol. 12, No. 4, Jul. 10, 1979, p. 40.

Primary Examiner—Edgar S. Burr
Assistant Examiner—Eric P. Raciti
Attorney, Agent, or Firm—Bernard J. Murphy

[57] ABSTRACT

In a first embodiment, the device is in the form of a face mask for affixing to the face of a patient to monitor the patient's respiration. It is self-powered and self-contained so that such respiration can be monitored all the while the patient is being transported. It incorporates light-emitting diodes which are illuminated, sequentially, to evidence regular breathing. When the patient stops breathing, the diodes do not illuminate, and an audible alarm is sounded to make medical personnel immediately aware of the breathing cessation.

12 Claims, 5 Drawing Sheets

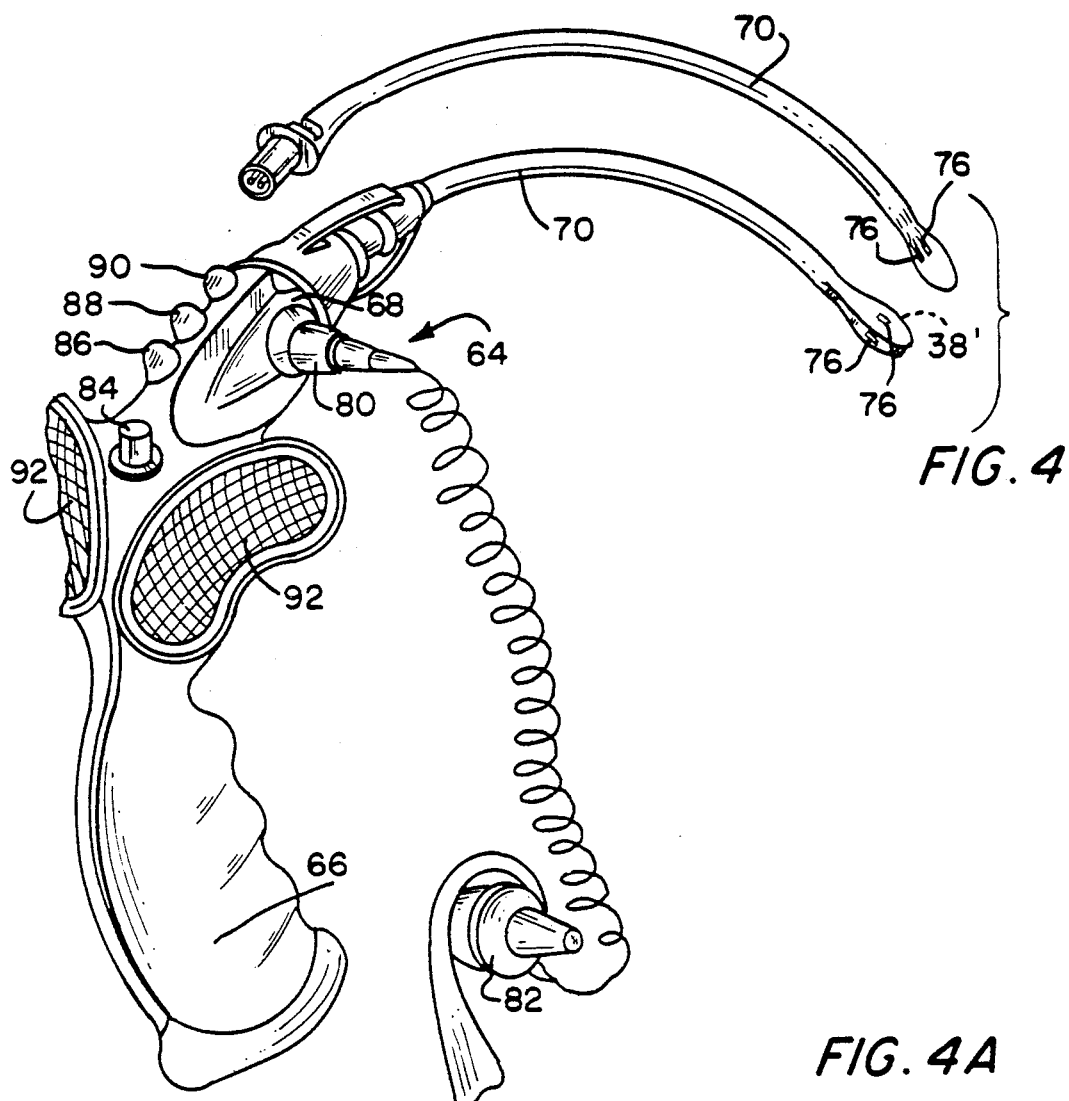
FIG. 4
FIG. 4A
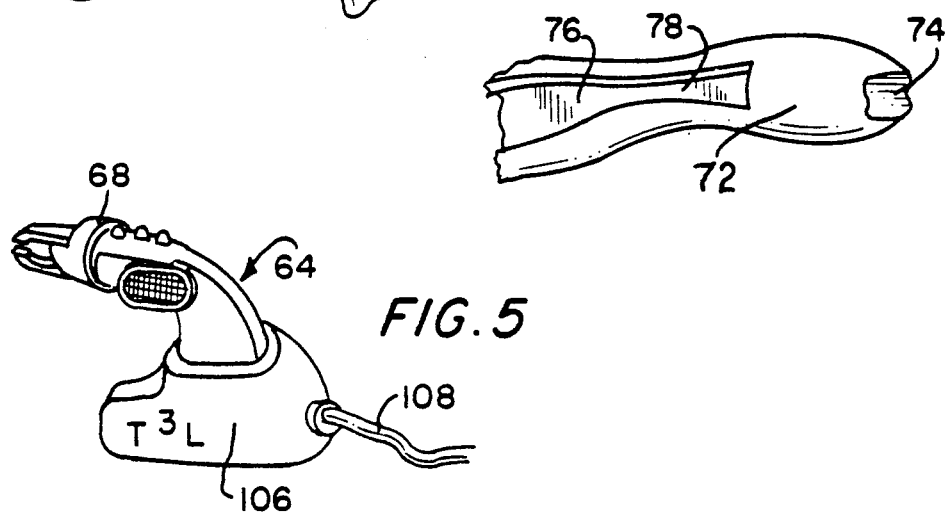
FIG. 5

RESPIRATION-SIGNALLING DEVICE

This invention pertains to respiration monitoring and/or detecting devices, and in particular to a novel respiration-signalling device.

In the prior art there are available respiration monitoring devices which are used with a bed-ridden patient to insure that the patient is manifesting normal breathing. However, what has been a long-sought need is a monitoring device which can signal respiration of a patient during transportation from an operating room to a recovery room; i.e., a portable, patient-worn respiration-signalling device for monitoring the patient's breathing.

Additionally, there is a need for a respiration-signalling device which can efficiently detect airflow in the trachea to positively locate the trachea for guiding an intubation tube for anesthesia.

It is an object of this invention to set forth a respiration-signalling device which meets the aforesaid needs.

Particularly, it is an object of this invention to set forth a respiration-signalling device comprising a housing; means coupled to said housing for admitting breath into said housing and discharging breath out of said housing; a sensory component coupled to said housing, and electrically-operative, for signalling respiration; electrically-operative means, coupled to said component, and responsive to respiration for operating said component; and a source of electrical potential coupled to said component-operating means for effecting operation thereof.

It is further an object of this invention to disclose a respiration-signalling device comprising a face mask; means for admitting breath into, and for discharging breath out of, said mask; first and second sensory components, coupled to said housing and electrically-operative, for signalling inspiration and expiration, respectively; first and second electrically-operative means, coupled to said first and second components, respectively, for operating said components; and a source of electrical potential coupled to both said first and second component-operating means for effecting operation thereof.

Further objects of this invention, as well as the novel features thereof, will become more apparent by reference to the following description, taken in conjunction with the accompanying figures, in which:

FIG. 4 is a perspective illustration of a second embodiment of the invention which takes the form of a trachea-locating handled probe;

FIG. 4A is a fragmentary view, considerably enlarged, of the end of the probe to show the air passages formed therein;

FIG. 5 is an illustration of the second embodiment of the invention set upon a battery charger when not in use;

Figure 1:
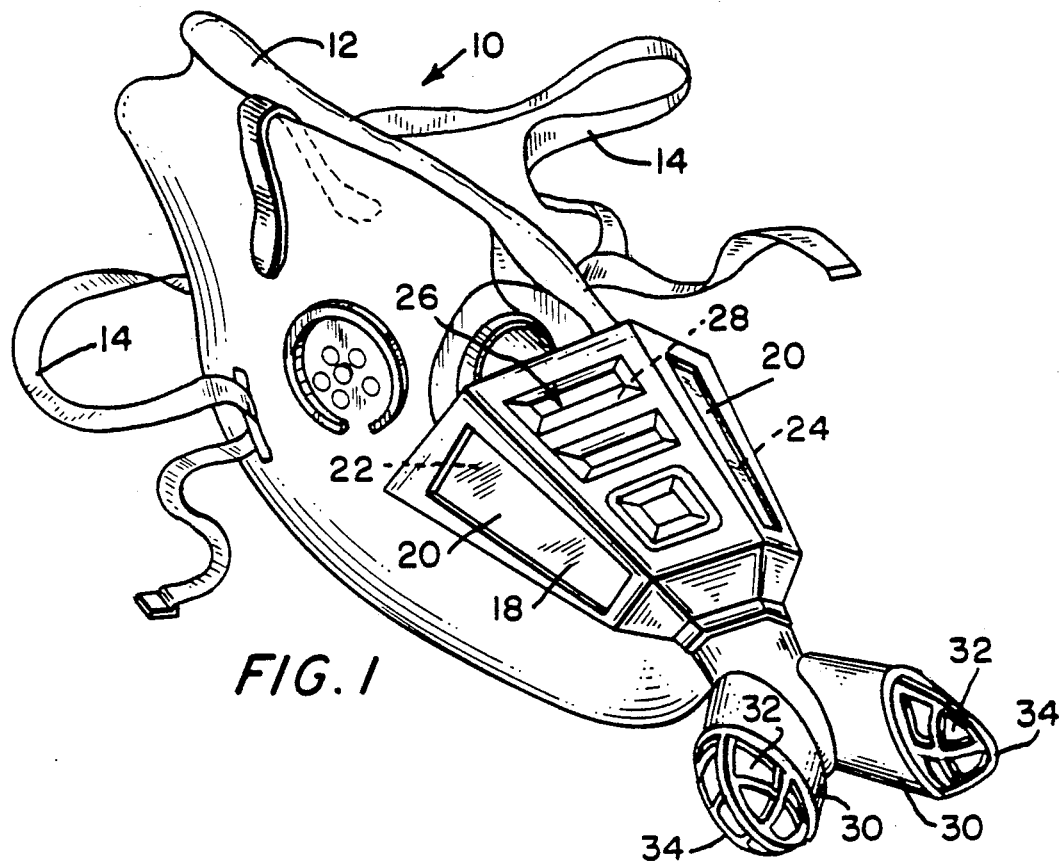
FIG. 1 is a perspective illustration of a first embodiment of the invention which takes the form of a face mask.
Figure 2:
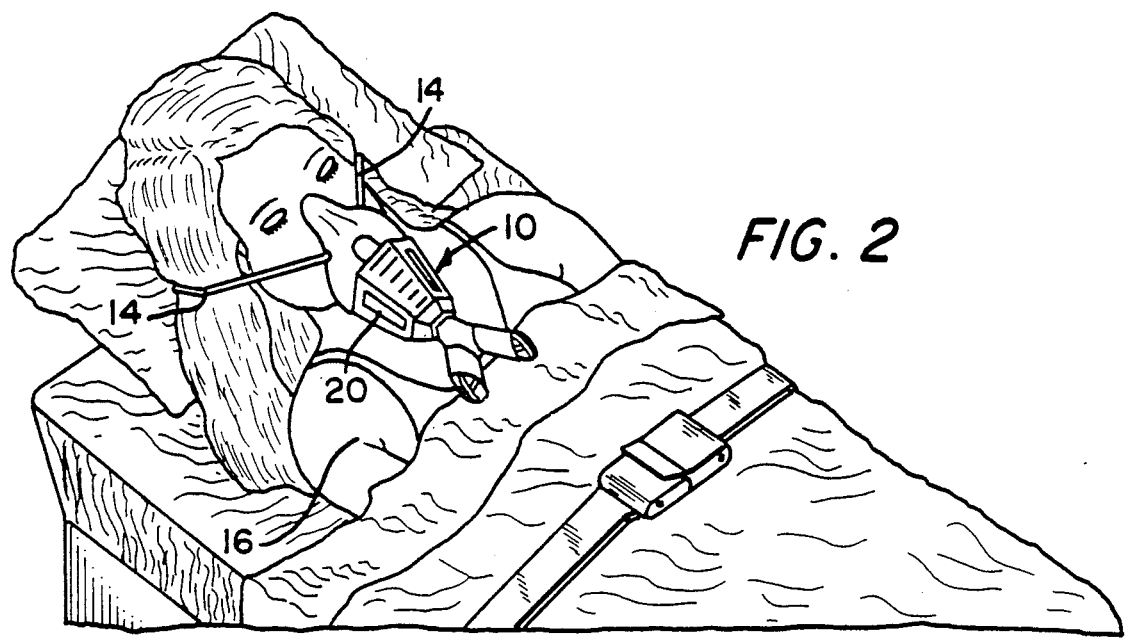
FIG. 2 is a depiction of the face mask of FIG. 1 in place on a patient during transport of the patient from surgery, or the like, to a recovery room.
Figure 3:
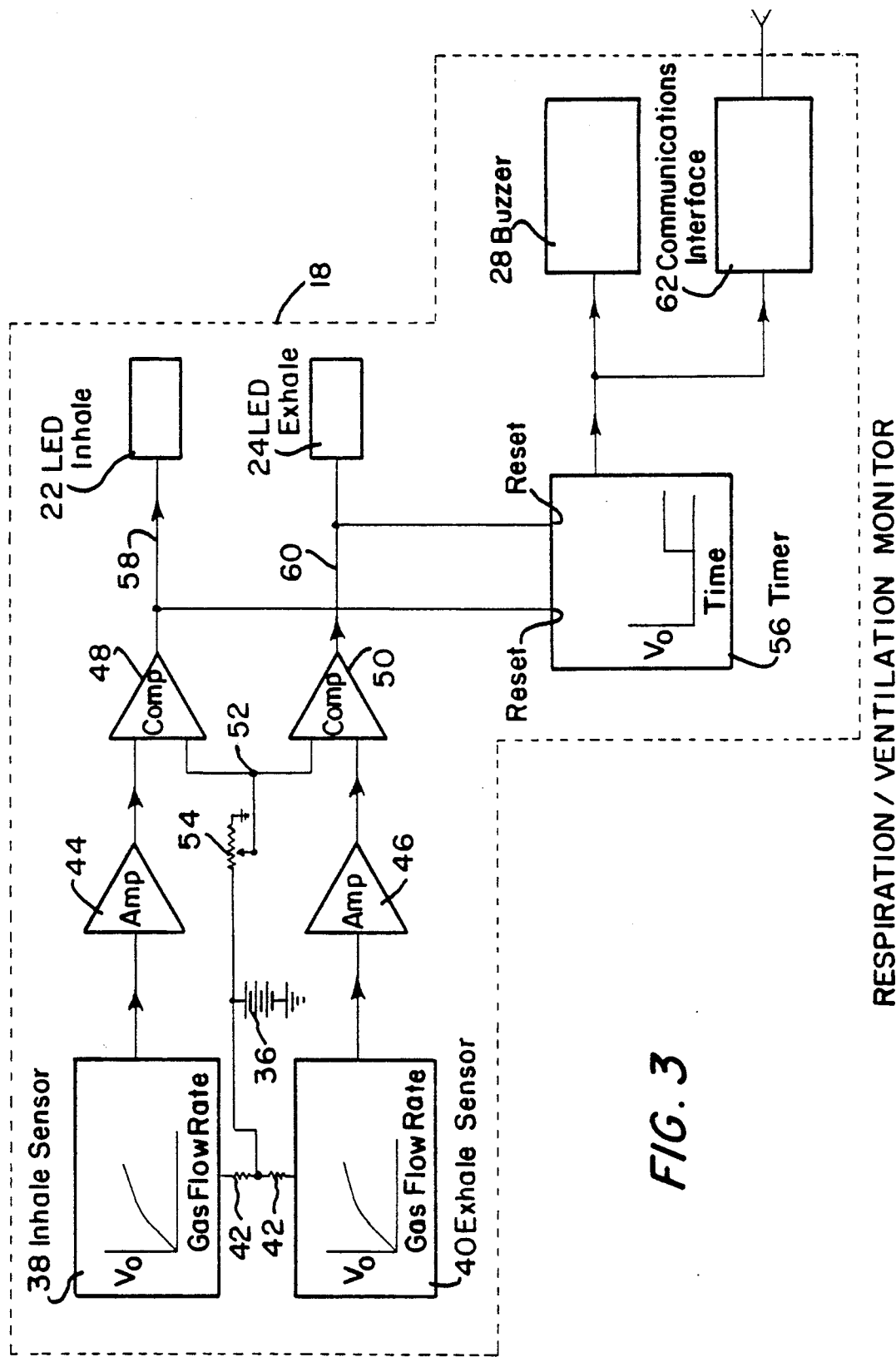
FIG. 3 is a block diagram of the circuitry of the first embodiment of the invention.

As shown in FIGS. 1-3, the first embodiment of the respiration-signalling device 10 comprises a face mask 12 having straps 14 for affixing thereof to the face of a patient 16. The mask 12 has a circuitry enclosure 18 for housing therewithin electrical components of the device. Enclosure 18 has a pair of lenses 20 behind which are light-emitting diodes 22 and 24 for evidencing normal breathing, as will be explained in the ensuing text. Too, the enclosure 18 has a louver 26 set over a buzzer 28 (therein) which will signal the cessation of breathing. At and end of the enclosure 18, supported on projecting lobes 30, are a pair of respiration openings 32, the latter having screens 34 fixed thereon.

The enclosure 18 contains a battery 36 which provides the electrical power for the device 10. An inspiration or inhale sensor 38, and an expiration or exhale sensor 40, each comprising a thermistor are coupled to the battery 36. The thermistor sensors 38 and 40 are heated to a stable level by current flowing through resistors 42 interposed between the sensors and the battery 36. Sensors 38 and 40 are independently coupled to voltage amplifiers 44 and 46. The latter, sequentially, are coupled to signal comparators 48 and 50. A threshold or reference level of potential is supplied to the comparators 48 and 50 by a common connection 52 via a potentiometer 54 which is coupled to the battery 36. Consequently, differential signals illuminate the diodes 22 and 24. Sensors 38 and 40 are heated, to achieve the aforesaid stable level, to a temperature above that of the patient's ingested and exhaled breath, and are disposed within the mask 12, for the passage of the patient's breathing thereacross. Sensor 38 is cooled, then, by the inhaled air, and sensor 40 is cooled by the exhaled air or breath. As a result, all the while that the patient is being transported, and experiencing normal breathing, the diodes 22 and 24 illuminate in proper sequence. The potentiometer 54 accommodates for the adjustment of the device 10 for heavy or shallow breathing. Of course, if there is a cessation of breathing, the diodes will fail to illuminate, and the buzzer 28 will sound to alert medical personnel to institute remedial action.

The buzzer 28 is activated by a timer 56 which receives signal outputs from lines 58 and 60, respectively, joined to diodes 22 and 24. The timer 56 monitors the breathing cycle as well, and has a pre-set response time, for example: five seconds. Hence, if either output, from lines 58 and 60, is absent for over five seconds, the timer 56 will operate to power the buzzer 28 and/or a communications interface 62 for signalling an external alarm device such as may be located in a nurses station, for instance.

An alternate embodiment 64 of a respiration-signalling device, depicted in FIGS. 4, 4A, 5 and 6, serves as a tracheal locating device. It comprises a handle 66 in which are confined the operating circuitry components. A projecting end 68 latchingly receives a tubular probe 70. One probe 70 is shown latched to the handle 66, and another is shown in isolation for purposes of clarity of perception. The remote end 72 of the probe 70 has a void 74 formed therein and a plurality of air guides 76 which define narrowed, venturi-like trackways 78 for inducing acceleration of respiration therethrough. Confined within the end 72 is a thermistor-sensor 38'. Electrical lines confined within the probe 70 couple the sensor 38' to the components within the handle 66. The handle end 68 has a socket 80 which receives an earphone 82 which may be used by a medical attendant. Carried atop the end 68 are an on/off switch 84, a low battery lamp 86, a light-emitting diode lens 88, a "ready" lamp 90, and a pair of speakers 92.

In use, the probe 70 is inserted through an intubation tube, and then into the mouth of the patient, and down into the trachea. It locates the trachea by sensing the gross airflow there and, consequently, provides for locating the intubation tube correctly thereat. Upon the probe 70 locating the trachea, the intubation tube is advanced thereto, and the probe 70 is then withdrawn (whereupon standard anesthesia equipment may be coupled to the intubation tube).

Figure 6:
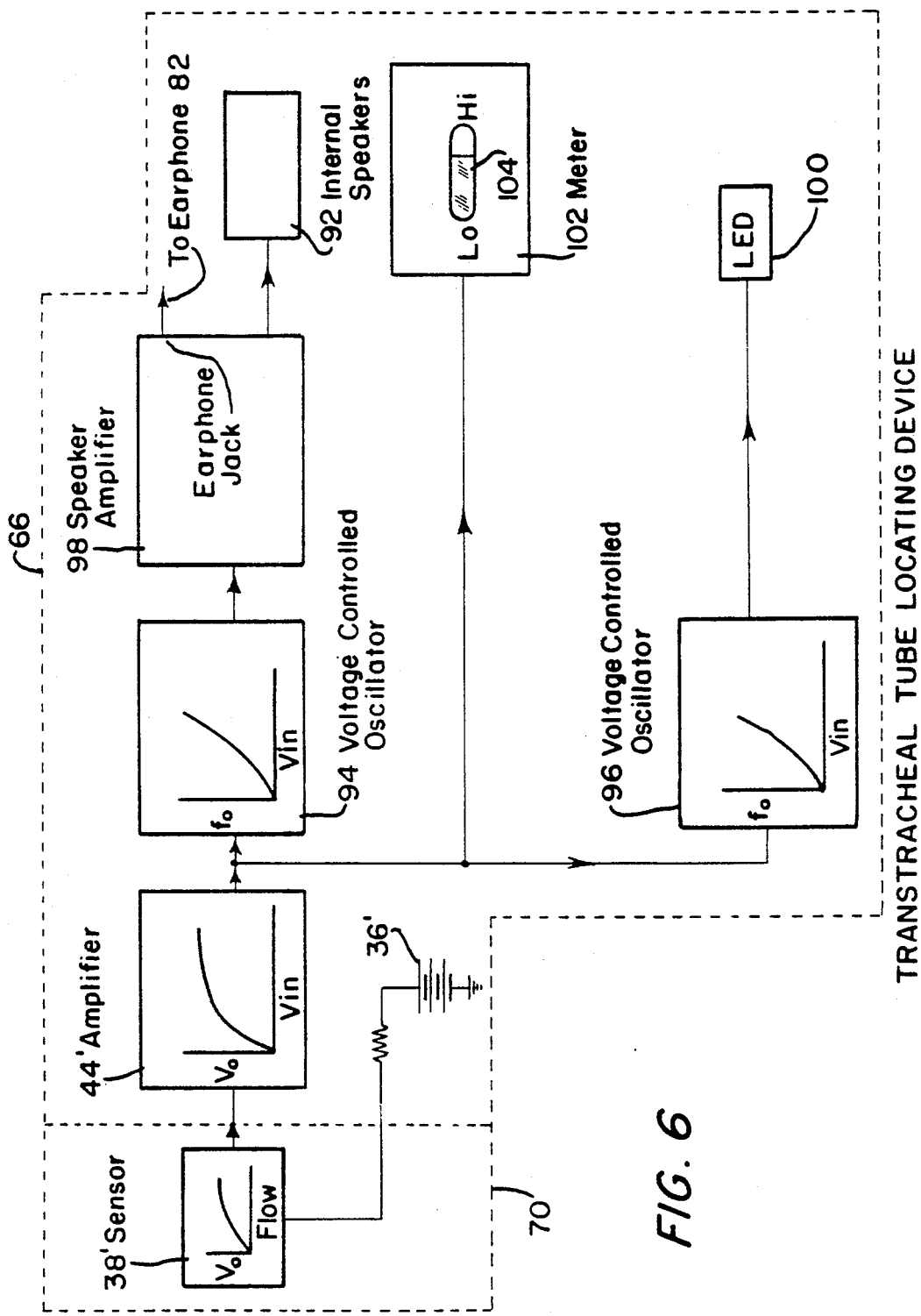
FIG. 6 is a block diagram of the circuitry of the second embodiment of the invention.

The handle-confined circuitry of FIG. 6 comprises another battery 36' which supplies current to the probe-carried thermistor-sensor 38'. The sensor 38' is coupled to another amplifier 44'. In this embodiment 64, what is provided is a signal frequency representative of the breathing or air flow into and out of the trachea. The sensor 38' provides a signal which varies with the air flow to the amplifier 44', which avoids saturation from heavy airflow, and, in turn, the signal is conducted to a pair of voltage-controlled oscillators 94 and 96. Oscillator 94 is coupled to a speaker amplifier 98. The latter supplies a signal, which increases in frequency with increasing airflow—indicative of a closure of the probe 70 onto the location of the trachea—to the speakers 92 and/or the earphone 82. The oscillator 96 supplies a same signal, which also increases in frequency with increasing airflow, to a light-emitting diode 100 (within lens 88). Oscillator 94 is configured to deliver an audio frequency, whereas oscillator 96 is configured to provide signal pulses within a range of zero to 25 pulses per second for visual perception. A further monitoring element, meter 102 having a reciprocating component 104 therewithin, is also coupled to the output of amplifier 44'. The component 104 is translatable within the meter 102 to track, and represent, the airflow in the trachea of the patient 16.

Embodiment 64 can be set into a battery recharger 106, as shown in FIG. 5, when not in use. The handle 66 has contactors (not shown) for engagement with receptors within the recharger 106, and the latter has a line cord 108, for attachement thereof to a source of voltage.

Figure 7:
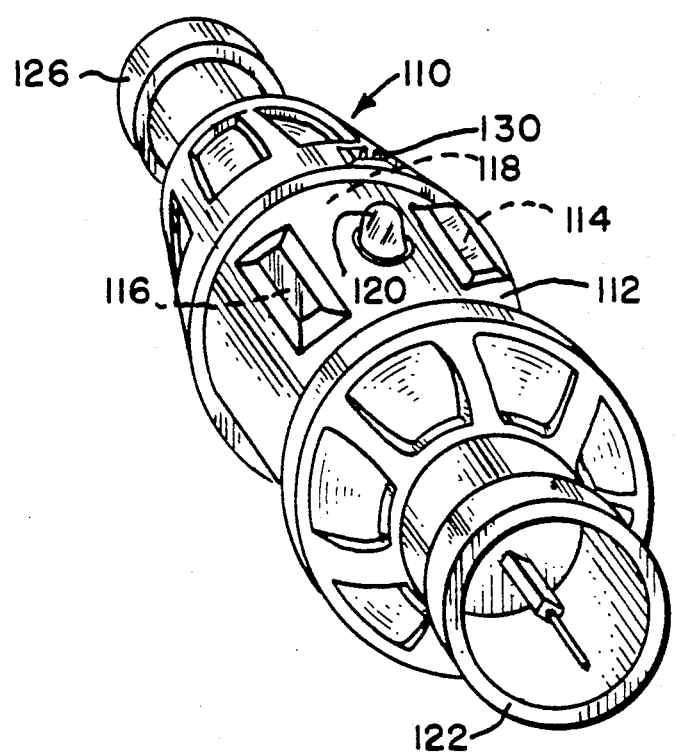
FIG. 7 is a perspective depiction of an embodiment of the novel respiration-signalling device for use with standard anesthesia equipment.
Figure 8:
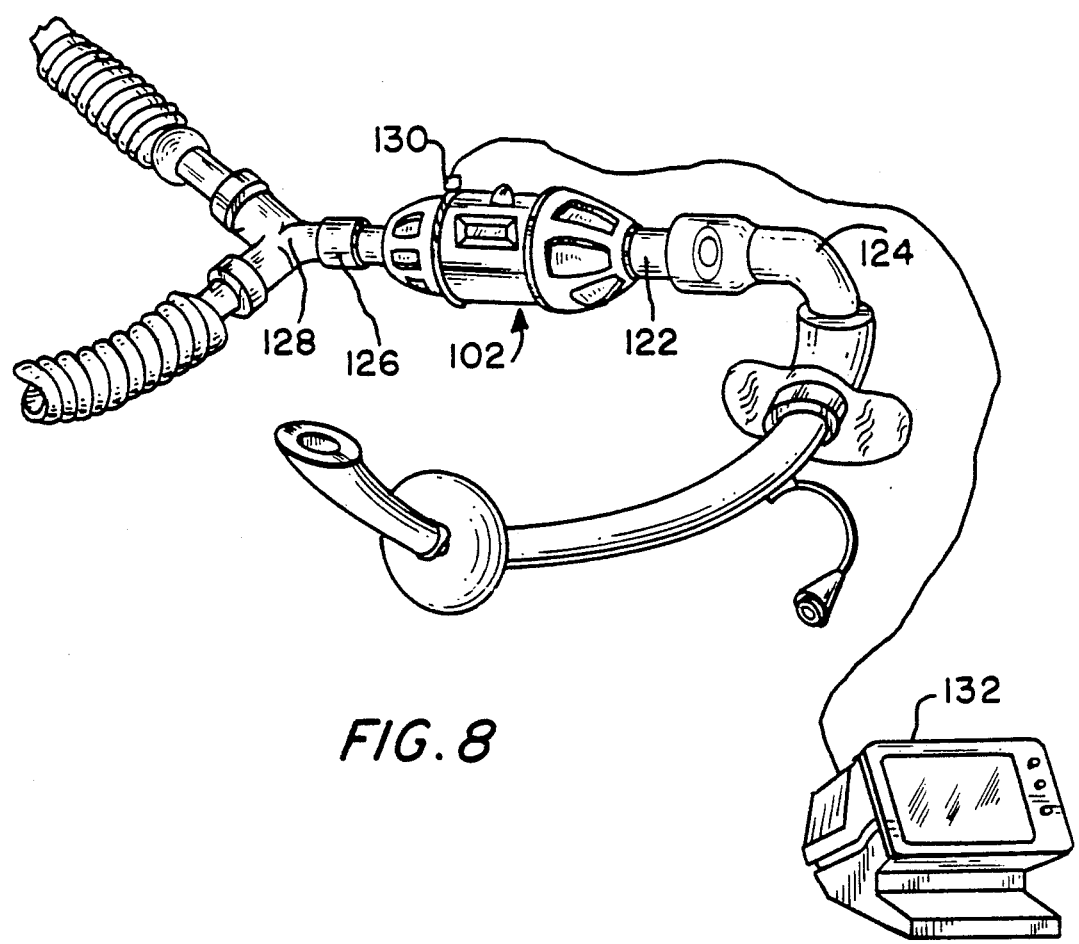
FIG. 8 depicts the embodiment of FIG. 7 in association with an intubation tube and anesthesia and oxygen tubes.

A further, alternative embodiment 110 of the invention is configured for incorporation with standard anesthesia equipment to constantly monitor a patient's respiration. The same is shown in FIG. 7, and in FIG. 8 in association with an intubation tube and anesthesia and oxygen tubes. Embodiment 110 comprises a housing 112 which confines the relevant circuitry to operate inhale and exhale light-emitting diodes 114 and 116, a battery 118 as a power source, as well as a low battery indicator 120. A collar 122 at one end receives an end of an intubation tube 124, and another collar 126 at the opposite end receives the Y-connector 128 of anesthesia and oxygen tubes. The housing 112 has a socket connection 130 which may be used for the attachment of an optional visual display unit 132. The operation of this embodiment 110 is identical to that of the embodiment 10 of FIGS. 1-3; only the housing 112 differs from the enclosure 18 of the first embodiment.

While the invention has been described in connection with specific embodiments thereof it is to be clearly understood that this is done only by way of example and not as a limitation to the scope of the invention as set forth in the objects thereof and in the appended claims.

We claim:

1. A respiration-signalling device, comprising:
   a housing; wherein
   said housing comprises a face mask;
   said face mask comprises (a) means for enclosing therewithin both the nasal and oral breathing passages of a patient, and (b) an electrical-circuitry enclosure;
   said enclosure confines therewithin a pair of thermistors which are disposed to accommodate a conduct of a patient's breathing thereacross;
   said enclosure further confines therewithin (a) a battery, and (b) means coupling said thermistors to said battery for heating of said thermistors to a stable temperature which is higher than the temperature of such patient's inhaled and exhaled breath;
   one thermistor of said pair thereof comprises means responsive to a conduct of such patient's exhaled breath thereacross to cause (a) a cooling of said one thermistor, and (b) an increase in electrical resistance of said one thermistor;
   the other thermistor of said pair thereof comprises means responsive to a conduct of such patient's inhaled breath thereacross to cause (a) a cooling of said other thermistor, and (b) an increase in electrical resistance of said other thermistor; and further including
   sensory indicator means also confined within said enclosure, and coupled to said thermistors, responsive to an increase in electrical resistance of said thermistors for providing a sensory indication of such patient's breathing performance.

2. A respiration-signalling device, according to claim 1, wherein:
   said sensory-indication means comprises a pair of light-emitting diodes.

3. A respiration-signalling device, according to claim 1, wherein:
   said sensory-indication means comprises means for producing an audible signal.

4. A respiration-signalling device, according to claim 2, wherein:
   said sensory-indication means comprises, further, means coupled to said thermistors for enhancing an electrical output of said thermistors.

5. A respiration-signalling device, according to claim 2, further including:
   voltage amplifiers interposed between said diodes and said thermistors.

6. A respiration-signalling device, according to claim 5, further including:
   signal comparators interposed between said voltage amplifiers and said diodes.

7. A respiration-signalling device, according to claim 3, wherein:
   said audible-signal producing means comprises a buzzer.

8. A respiration-signalling device, according to claim 7, further including:
   timing means, interposed between said buzzer and said thermistors, for controlling operation of said buzzer.

9. A respiration-signalling device, comprising:

a housing having (a) a handle, and (b) an elongate probe; wherein said elongate probe confining therewithin a thermistor, and further comprises means for conducting a patient's breathing across said thermistor;

said housing further confines therewithin (a) a battery, and (b) means coupling said thermistor to said battery for causing said battery to heat said thermistor to a stable temperature which is higher than the temperature of such patient's inhaled and exhaled breath; and said thermistor comprises means responsive to a conduct of such patient's breathing thereacross to cause (a) cooling of said thermistor, and (b) an increase in electrical resistance of said thermistor; and further including sensory-indication means also confined within said housing, and coupled to said thermistor, responsive to an increase in electrical resistance of said thermistor for providing a sensory indication of such patient's breathing performance;

and a voltage controlled oscillator interposed between said thermistor and said sensory-indication means.

10. A respiration-signalling device, according to claim 9, wherein:

said sensory-indication means comprises a light-emitting diode; and further including a voltage amplifier interposed between said oscillator and said thermistor.

11. A respiration-signalling device, according to claim 9, wherein:

said sensory-indication means comprises a speaker-amplifier.

12. A respiration-signalling device, according to claim 11, further including a voltage amplifier interposed between said oscillator and said thermistor.

* * * * *